United States Patent
Bigner et al.

(10) Patent No.: US 10,744,170 B2
(45) Date of Patent: Aug. 18, 2020

(54) COMBINATION TREATMENT

(71) Applicant: Duke University, Durham, NC (US)

(72) Inventors: Darell D. Bigner, Mebane, NC (US); Matthias Gromeier, Durham, NC (US); Smita Nair, Cary, NC (US); Vidyalakshmi Chandramohan, Durham, NC (US)

(73) Assignee: Duke University, Durham, NC (US)

(*) Notice: Subject to any disclaimer, the term of this patent is extended or adjusted under 35 U.S.C. 154(b) by 145 days.

(21) Appl. No.: 15/768,147

(22) PCT Filed: Oct. 14, 2016

(86) PCT No.: PCT/US2016/057023
§ 371 (c)(1),
(2) Date: Apr. 13, 2018

(87) PCT Pub. No.: WO2017/066557
PCT Pub. Date: Apr. 20, 2017

(65) Prior Publication Data
US 2018/0296614 A1    Oct. 18, 2018

Related U.S. Application Data

(60) Provisional application No. 62/361,725, filed on Jul. 13, 2016, provisional application No. 62/356,831, filed on Jun. 30, 2016, provisional application No. 62/242,123, filed on Oct. 15, 2015.

(51) Int. Cl.

| | | |
|---|---|---|
| *A61K 35/768* | (2015.01) | |
| *A61K 39/13* | (2006.01) | |
| *A61K 39/395* | (2006.01) | |
| *A61K 9/127* | (2006.01) | |
| *A61P 35/00* | (2006.01) | |
| *C07K 16/28* | (2006.01) | |
| *C12N 15/85* | (2006.01) | |
| *A61K 39/39* | (2006.01) | |
| *C12N 7/00* | (2006.01) | |
| *A61K 39/00* | (2006.01) | |

(52) U.S. Cl.
CPC ............ *A61K 35/768* (2013.01); *A61K 9/127* (2013.01); *A61K 39/13* (2013.01); *A61K 39/39* (2013.01); *A61K 39/39541* (2013.01); *A61P 35/00* (2018.01); *C07K 16/2818* (2013.01); *C12N 7/00* (2013.01); *C12N 15/85* (2013.01); *A61K 2039/505* (2013.01); *A61K 2300/00* (2013.01); *C07K 2317/76* (2013.01); *C12N 2770/32621* (2013.01); *C12N 2770/32632* (2013.01); *C12N 2840/203* (2013.01); *Y02A 50/466* (2018.01)

(58) Field of Classification Search
None
See application file for complete search history.

(56) References Cited

U.S. PATENT DOCUMENTS 8,066,983 B2    11/2011    Wimmer et al.

FOREIGN PATENT DOCUMENTS

| JP | 2015508156 A | 3/2015 |
|---|---|---|
| WO | 2013112942 A1 | 8/2013 |
| WO | 2014047350 A1 | 3/2014 |
| WO | 2014-081937 A2 | 5/2014 |
| WO | 2015-069770 A1 | 5/2015 |
| WO | 2015-103602 A1 | 7/2015 |
| WO | 2015127501 A1 | 9/2015 |

OTHER PUBLICATIONS

Madjd, et al. (2004) "Loss of CD55 Is Associated with Aggressive Breast Tumors", Clinical Cancer Research, 10: 2797-803. (Year: 2004).*
Jackson, et al. (Apr. 25, 2014) "Immunotherapy for Brain Cancer: Recent Progress and Future Promise", Clinical Cancer Research, 20(14): 3651-59. (Year: 2014).*
Goetz, et al. (2011) "Oncolytic poliovirus against malignant glioma", Future Virology, 6(9): 1045-58 (obtained as NIH Public Access Author Manuscript, 22 pages long). (Year: 2011).*
Engeland et al. "CTLA-4 and PD-L1 Checkpoint Blockade Enhances Oncolytic Measles Virus Therapy" Molecular Therapy, vol. 22, No. 11, 1949-1959, Nov. 2014.
Quetglas et al. "Immunotherapeutic Synergy Between Anti-CD137 mAb and Intratumoral Administration of a Cytopathic Semliki Forest Virus Encoding IL-12" Molecular Therapy, vol. 20, No. 9, 1664-1675, 2012.
Saishin Igaku ("The Medical Frontline"), Mar. 2015, vol. 70, No. 3, pp. 378-385.
Lowther et al. "The TIGIT/CD226/CD155 axis is differentially expressed in MS and glioblastoma: implications for autoimmunity and tumor immune escape. (P4.043)" Neurology, Apr. 2015, vol. 84, supplement 14, Abstract No. P4.043.
Apr. 15, 2019—(JP) Office Action—App 2018—519304—English Translation.
John et al. "Oncolytic Virus and Anti-4-1BB Combination Therapy Elicits Strong Antitumor Immunity against Establised Cancer" Cancer Research, vol. 72, No. 7, pp. 1651-1660, Feb. 7, 2012.
Ruotsalainen "Interferon Response as a Challenge and Possibility for Developing Alphavirus Based Oncolytic Virotherapy" Sep. 26, 2015, retrieved from the internet: url:http://epublications.uef.fi.pub.urn_isbn_978-952-61-1555-9/urn_isbn_978-952-61-1555-9.pdf, Dissertations in Health Sciences, Publications of the University of Eastern Finland, No. 247, pp. 1-105.

(Continued)

*Primary Examiner* — Robert M Kelly
(74) *Attorney, Agent, or Firm* — Banner & Witcoff, Ltd.

(57) ABSTRACT

Human clinical use of a chimeric poliovirus construct has demonstrated excellent anti-tumor effect. Combination with immune checkpoint inhibitors increases the anti-tumor effect. Tumors of different types are susceptible to the combination treatment, including but not limited to melanoma, glioblastoma, renal cell carcinoma, prostate cancer, breast cancer, lung cancer, medulloblastoma, and colorectal cancer.

27 Claims, 6 Drawing Sheets

(56) References Cited

OTHER PUBLICATIONS

Kaufman et al. "Oncolytic viruses: a new class of immunotherapy drugs" Nature Reviews, vol. 14, No. 9, pp. 642-662, Sep. 1, 2015.
Dias et al. "Targeted cancer immunotherapy with oncolytic adenovirus coding for a fully human monoclonal antibody specific for CTLA-4" Gene Therapy, vol. 19, No. 10, pp. 988-998, Nov. 10, 2011.
Zamarin et al. "Localized Oncolytic Virotherapy Overcomes Systemic Tumor Resistance to Immune Checkpoint Blockade Immunotherapy" Science Translational Medicine, vol. 6, No. 226, pp. 1-11, Mar. 5, 2014.
Mar. 25, 2019—(EP) Extended European Search Report—App 16856268.4.
Bell "Oncolytic Viruses: Immune or Cytolytic Therapy?" Molecular Therapy, vol. 22, No. 7, pp. 1231-1232, Jul. 1, 2014.
Brown et al. "Oncolytic Polio Virotherapy of Cancer" Cancer, vol. 120, No. 21, pp. 3277-3286, Nov. 1, 2014.
Brown et al. "Cytotoxic and Immunogenic Mechanisms of Recombinant Oncolytic Poliovirus" Current Opinion in Virology, vol. 13, pp. 81-85, Aug. 1, 2015.
Walker, "Smita Nair, PhD, to Lead Study of Novel Oncolytic Poliovirus Immunotherapy in Breast Cancer" Retrieved from the Internet: URL: https://surgery.duke.edu/news/smita-nair-phd-lead-study-novel-oncolytic-poliovirus-immunotherapy-breast-cancer, pp. 1-4, Dec. 8, 2015.
Apr. 1, 2020 (JP) Decision of Rejection—Appl 2018—519304.
Turnis et al. "Inhibitory receptors as targets for cancer immunotherapy" Eur. J. Immunol.; Jul. 2015; 45(7) 1892-1905.
Antonarakis, E., 'Combining active immunotherapy with immune checkpoint bloackade for the treatment of advanced prostate cancer' Asian Journal of Andrology, 2012, vol. 14, pp. 520-521 See p. 520.
International Search Report for PCT/US2016/057023 [dated Jan. 11, 2017].

\* cited by examiner

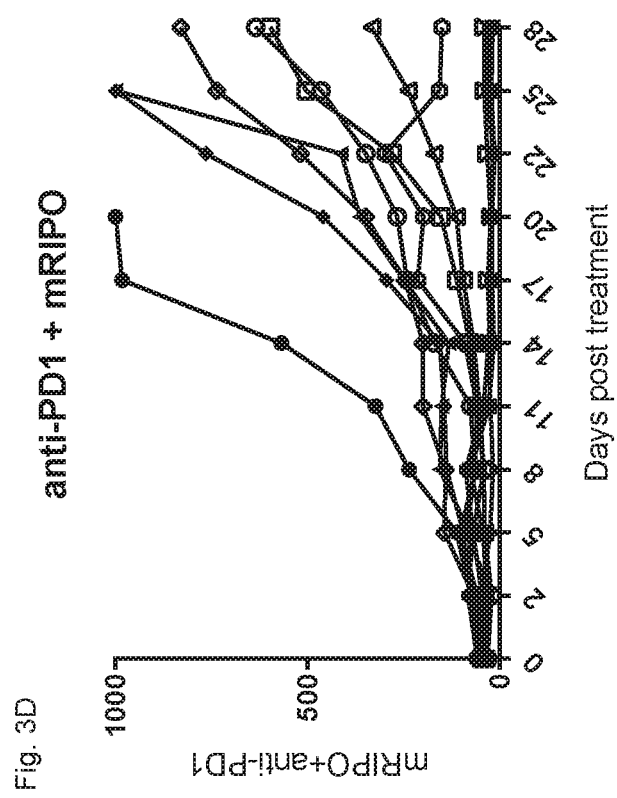

COMBINATION TREATMENT

This invention was made using funds provided by the United States government. The U.S. government retains certain rights according to the terms of grants from the National Institutes of Health R01 CA87537, P50 NS20023, P50 CA190991, R01 CA124756, and R01 CA140510.

TECHNICAL FIELD OF THE INVENTION

This invention is related to the area of anti-tumor therapy. In particular, it relates to oncolytic virus anti-tumor therapy.

BACKGROUND OF THE INVENTION

PVS-RIPO is an oncolytic poliovirus (PV) recombinant. It consists of the live attenuated type 1 (Sabin) PV vaccine containing a foreign internal ribosomal entry site (IRES) of human rhinovirus type 2 (HRV2). The IRES is a cis-acting genetic element located in the 5' untranslated region of the PV genome, mediating viral, $m^7G$-cap-independent translation. The virus has shown exciting signs of efficacy in humans. Nonetheless there is a continuing need in the art to identify and develop anti-cancer treatments that are more effective and that are effective for more humans, particularly for patients with brain tumors.

SUMMARY OF THE INVENTION

According to one aspect of the invention a method of treating a tumor in a patient is provided. A chimeric poliovirus construct is administered to the patient. The construct comprises a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame. An immune checkpoint inhibitor is also administered to the patient, either at the same time or within about 30 days.

According to another aspect of the invention a kit is provided for treating a tumor. The kit comprises a chimeric poliovirus construct comprising a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame; and an immune checkpoint inhibitor.

According to a further aspect of the invention, provided is a combination of a chimeric poliovirus construct and an immune checkpoint inhibitor for use as a medicament, or for use in treating a tumor, wherein the chimeric poliovirus construct comprises a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame; and an immune checkpoint inhibitor.

These and other aspects which will be apparent to those of skill in the art upon reading the specification provide the art with new therapeutic regimens for treating cancer.

BRIEF DESCRIPTION OF THE DRAWINGS

FIGS. 3A-3D show result of in vivo testing in mouse tumor model using CT2A gliomas in C57B16 mice; both the mice and the CT2A cells express the human poliovirus receptor CD155. Results (tumor volume over time) with the following experimental treatments are shown in FIG. 3A: Group I (▼): DMEM (vehicle to control for virus)+IgG (to control for anti-PD1); Group II (●): single intra-tumoral injection of PVSRIPO +IgG; Group III (▲): single intra-tumoral injection of DMEM+anti-PD1; Group IV (■): single intra-tumoral injection of PVSRIPO+anti-PD1. Anti-PD1 was given in three installments (days 3, 6, 9) by intraperitoneal injection. FIGS. 3B-3D show tumor responses (tumor volume over time) in individual treated mice (each line a different mouse) in the treatment groups II-IV.

DETAILED DESCRIPTION OF THE INVENTION

Figure 1:
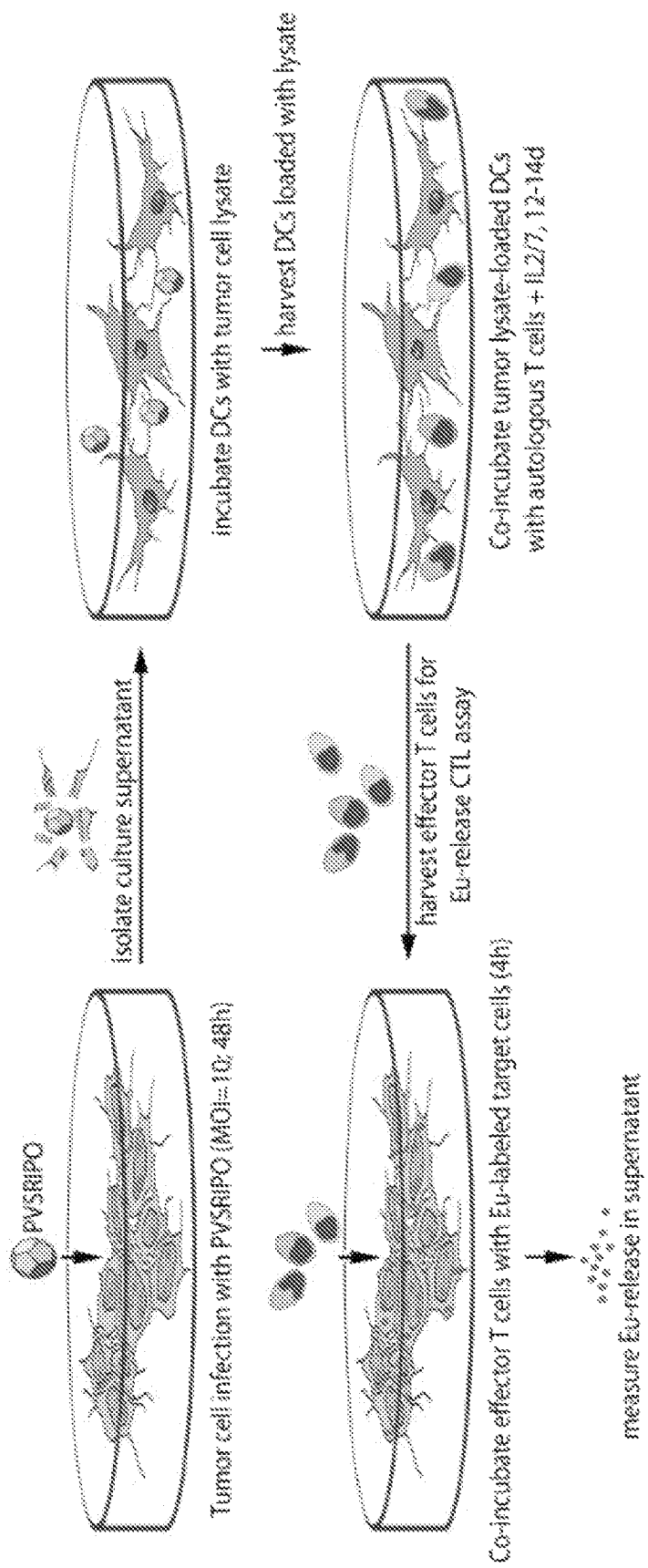
FIG. 1 depicts experimental schema.

The inventors have developed a combination therapy regimen in which a viral construct and an immune checkpoint inhibitor are administered to humans. Because the poliovirus is a potential disease agent, extra precautions must be taken to ensure that disease-causing agents are not introduced to the subjects. Using good manufacturing procedures and purifications, a preparation was made that was sufficiently pure to permit introduction into humans.

Any technique for directly administering the viral preparation to the tumor may be used. Direct administration does not rely on the blood vasculature to access the tumor. The preparation may be painted on the surface of the tumor, injected into the tumor, instilled in or at the tumor site during surgery, infused into the tumor via a catheter, etc. One particular technique which may be used is convection enhanced delivery.

Immune checkpoint inhibitors which may be used according to the invention are any that disrupt the inhibitory interaction of cytotoxic T cells and tumor cells. These include but are not limited to anti-PD-1 antibody, anti-PD-L1 antibody, anti-CTLA4 antibody, anti-LAG-3 antibody, and/or anti-TIM-3 antibody. Approved checkpoint inhibitors in the U.S. include ipimilumab, pembrolizumab, and nivolumab. The inhibitor need not be an antibody, but can be a small molecule or other polymer. If the inhibitor is an antibody it can be a polyclonal, monoclonal, fragment, single chain, or other antibody variant construct. Inhibitors may target any immune checkpoint known in the art, including but not limited to, CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and the B-7 family of ligands. Combinations of inhibitors for a single target immune checkpoint or different inhibitors for different immune checkpoints may be used. Additionally, CSF-1R blockade may be used in combination or as an alternative to immune checkpoint inhibitor(s), to ensure generation of potent and sustained immunity that effectively eliminates distant metastases and recurrent tumors. Antibodies specific for CSF-1R or drugs that inhibit or blockade CSF-1R may be used for this purpose, including but not limited to imactuzumab and AMG820.

The immune checkpoint inhibitor may be administered at the same time, before, or after the poliovirus. Typically the two agents will be administered within 30, 28, 21, 14, 7, 4, 2, or 1 day(s) of each other. The agents may be given repeatedly, either serially or in a cycle of first and second agents. It may be advantageous but not necessary for the vaccine to be administered prior to the checkpoint inhibitor. But the reverse order may also be used. Priming of a cytotoxic T lymphocyte response by the viral construct may take from about 5 to about 14 days. Administration of the checkpoint inhibitor may beneficially be commenced during or after the priming period.

Immune checkpoint inhibitors may be administered by any appropriate means known in the art for the particular inhibitor. These include intravenous, oral, intraperitoneal, sublingual, intrathecal, intracavitary, intramuscularly, and subcutaneously. Optionally, the immune checkpoint inhibitor may be administered in combination with the poliovirus agent.

Any human tumor can be treated, including both pediatric and adult tumors. The tumor may be in any organ, for example, brain, prostate, breast, lung, colon, and rectum, Various types of tumors may be treated, including, for example, glioblastoma, medulloblastomas, carcinoma, adenocarcinoma, etc. Other examples of tumors include, adrenocortical carcinoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, breast sarcoma, bronchial cancer, bronchoalveolar carcinoma, cervical cancer, craniopharyngioma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gall bladder cancer, gastric cancer, gastrointestinal carcinoid tumor, gastrointestinal stromal tumor, gestational trophoblastic tumor, gestational trophoblastic tumor, glioma, head and neck cancer, hepatocellular cancer, Hilar cholangiocarcinoma, hypopharyngeal cancer, intraocular melanoma, islet cell tumor, Kaposi sarcoma, Langerhans cell histiocytosis, large-cell undifferentiated lung carcinoma, laryngeal cancer, lip cancer, lung adenocarcinoma, malignant fibrous histiocytoma, medulloepithelioma, melanoma, Merkel cell carcinoma, mesothelioma, endocrine neoplasia, nasal cavity cancer, nasopharyngeal cancer, neuroblastoma, oral cancer, oropharyngeal cancer, osteosarcoma, ovarian clear cell carcinoma, ovarian epithelial cancer, ovarian germ cell tumor, pancreatic cancer, papillomatosis, paranasal sinus cancer, parathyroid cancer, penile cancer, pharyngeal cancer, pineal parenchymal tumor, pineoblastoma, pituitary tumor, pleuropulmonary blastoma, renal cell cancer, respiratory tract cancer with chromosome 15 changes, retinoblastoma, rhabdomyosarcoma, salivary gland cancer, small cell lung cancer, small intestine cancer, soft tissue sarcoma, squamous cell carcinoma, squamous non-small cell lung cancer, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, and Wilms tumor.

Optionally, patients may be stratified on the basis of NECL5 (poliovirus receptor) expression. This can be assayed at the RNA or protein level, using probes, primers, or antibodies, for example. The NECL5 expression may guide the decision to treat or not treat with the chimeric poliovirus of the present invention. The NECL5 expression may also be used to guide the aggressiveness of the treatment, including the dose, frequency, and duration of treatments. Antibodies to NECL5 (CD155) are commercially available and may be used. NECL5 RNA expression can also be assayed. See Hirota et al. *Oncogene* 24:2229-2235 (2005).

Treatment regimens may include, in addition to delivery of the chimeric poliovirus construct and immune checkpoint inhibitor combination, surgical removal of the tumor, surgical reduction of the tumor, chemotherapy, biological therapy, radiotherapy. These modalities are standard of care in many disease states, and the patient need not be denied the standard of care. The chimeric poliovirus and immune checkpoint inhibitor combination may be administered before, during, or after the standard of care. The chimeric poliovirus and immune checkpoint inhibitor combination may be administered after failure of the standard of care. When a combination is specified, it may be administered separately in time as two separate agents within a single combination regimen. Alternatively, the two (or more) agents may be administered in admixture.

Kits may comprise, in a single divided or undivided container, both the chimeric poliovirus construct PVSRIPO as well as a checkpoint inhibitor. They two may be in separate vessels or in a single vessel in admixture. Instructions for administration may be included. Optionally, an antibody for testing NECL5 expression in the patient is a component of the kit.

Applicants have found that the clinical pharmaceutical preparation of the chimeric poliovirus has admirable genetic stability and homogeneity. This is particularly advantageous as the poliovirus is known to be highly mutable both in culture and in natural biological reservoirs. Any suitable assay for genetic stability and homogeneity can be used. One assay for stability involves testing for the inability to grow at 39.5 degrees C. Another assay involves bulk sequencing. Yet another assay involves testing for primate neurovirulence.

While applicants do not wish to be bound by any particular mechanism of action, it is believed that multiple mechanisms may contribute to the efficacy of the poliovirus construct. These include lysis of cancer cells, recruitment of immune cells, and specificity for cancer cells. Moreover, the virus is neuro-attenuated.

The above disclosure generally describes the present invention. All references disclosed herein are expressly incorporated by reference. A more complete understanding can be obtained by reference to the following specific examples, which are provided herein for purposes of illustration only, and are not intended to limit the scope of the invention.

Example 1

Animal Tumor Models.

An IND-directed efficacy trial of PVS-RIPO was conducted in the HTB-15 GBM xenograft model in athymic mice. PVS-RIPO (from the clinical lot) was administered at the 'mouse-adjusted', FDA-approved max. starting dose [the FDA-approved max. starting dose (10e8 TCID) was adjusted for the reduced tumor size in mice (to $6.7 \times 10e6$ TCID)]. Delivery mimicked the intended clinical route, i.e., slow intratumoral infusion. Under these conditions, PVS-RIPO induced complete tumor regress in all animals after 15 days. While virus was recovered from treated tumors until day 10, the levels were modest at best, indicating that direct viral tumor cell killing alone cannot account for the treatment effect.

Evidence from animal tumor models suggests that intratumoral inoculation of PVS-RIPO causes direct virus-induced tumor cell killing and elicits a powerful host immunologic response against the infected/killed tumor (3, 7, 10). The response to virus infusion is characterized by a strong, local inflammatory response, leading to immune infiltration of the tumor. Eventually the slow tissue response to PVS-RIPO infusion leads to the demise of the tumor mass and its replacement by a scar.

Example 2

Clinical Trials.

IND no. 14,735 'Dose-finding and Safety Study of PVS-RIPO Against Recurrent Glioblastoma' was FDA-approved on Jun. 19, 2011 and IRB-approved on Oct. 27, 2011. A phase I/II clinical trial in patients with recurrent glioblastoma (GBM) (NCT01491893) is currently enrolling patients.

Two human subjects have so far been treated with PVS-RIPO per IRB-approved protocol. Preliminary findings from the first subject are described in Example 3.

Example 3

Preliminary Findings with First Human Subject.

The patient is a 21-year-old female nursing student diagnosed with a right frontal GBM (WHO grade IV). She was first diagnosed in June/2011, at the age of 20 years, following a history of severe headaches and unsuccessful treatment for a suspected sinus infection. Brain imaging was obtained on Jun. 17, 2011 and showed a large right frontal mass, measuring ~5×6 cm. She underwent a subtotal resection of the right frontal mass on Jun. 22, 2011, with pathology confirming GBM (WHO grade IV). Given the young age of the patient, her excellent performance status and the subtotal tumor resection, it was decided to treat her aggressively with a combination of six weeks of radiation therapy with concurrent Temodar chemotherapy at 75 mg/m$^2$ by mouth daily and bevacizumab (antiangiogenic agent) administered every 2 weeks. The patient completed six weeks of treatment on Sep. 18, 2011. On Oct. 3, 2011, the patient initiated adjuvant therapy with monthly, five-day Temodar chemotherapy in addition to bevacizumab 10 mg/kg every two weeks.

On Apr. 16, 2012, the patient presented to clinic after having experienced her first generalized seizure, which occurred in her sleep. By that time, she had completed six months of the combination of Temodar and bevacizumab. She had attributed the seizure to increased stress at school, as she was completing a degree to become a pediatric oncology nurse, despite her diagnosis of GBM and ongoing chemotherapy treatment. The brain MRI obtained on that day showed tumor recurrence, with a new nodular enhancement along the medial aspect of the resection cavity (FIG. 12).

The patient was offered multiple treatment options, but elected to pursue the PVS-RIPO clinical trial. Following her first generalized seizure, she was initiated on Keppra, but forgot to take it on occasion and because of this and the known tumor recurrence, the patient experienced a second generalized seizure in her sleep on May 6, 2012. She went back to her baseline neurologic condition and was worked up to enroll on protocol.

A follow-up MRI was obtained on May 9, 2012 (FIG. 13), before the patient underwent infusion of PVS-RIPO on May 11, 2012 with the FDA-approved max. starting dose (10e8) by the intended clinical delivery method (convection-enhanced, intratumoral infusion of 3 mL of virus suspension containing the contrast Gd-DTPA over 6 hrs; see Example 4) and experienced no neurologic or other complications related to this.

An MRI obtained immediately after completion of the infusion documents the distribution of the infusate (FIG. 14).

Our research team followed up on the patient on a weekly basis and she was seen in clinic two weeks post infusion, at which time she denied any new neurologic symptoms, seizure recurrence, fatigue, shortness of breath or weakness. She again was evaluated in clinic on Jun. 7, 2012 and her physical and neurological conditions remained normal. The brain MRI obtained at that visit showed stability of the disease (FIG. 15).

The patient was seen in clinic on Jul. 9, 2012. Once more, she denied any new neurologic symptoms, including the absence of any recurrent seizure activity since the seizure observed on May 6, 2012, prior to PVS-RIPO infusion. She also reported that her mood was good, that she was content with her progress in nursing school, feeling that she is able to focus in school much better since after her infusion. She was also excited by her move with two roommates and by the fact that she is able to exercise regularly. Her brain MRI obtained on that day showed a slightly increased mass effect and minimal increase in superior linear enhancement, concerning for progression of disease (FIG. 16).

In view of worrisome radiographic changes with no clinical worsening, we decided to obtain an 18-FDG PET scan. The 18-FDG PET scan demonstrated hypometabolic activity in the area of concern on the MRI, suggestive of a necrotic process (treatment response effect; FIG. 17). The PET scan from July 9 suggests the absence of viable tumor. After discussion with the patient and her mother, it was decided to continue to follow the patient from a clinical and radiographic standpoint.

In check-ups on August 27 and October 22 the patient denied any new neurologic symptoms, including the absence of any seizure activity since the seizure on May 6, 2012 (prior to PVS-RIPO infusion). The patient reports improved cognitive/memory function, motor function (exercise). As of October 26, the patient is neurologically normal.

Because of the favorable radiographic presentation at August 27, a PET scan was not ordered. The patient was re-scanned on October 22 and there was a quantifiable radiographic response.

An MRI/PET overlay demonstrates the absence of signal from the general area of the tumor recurrence.

Example 4

Convection Infusion.

Preoperatively the BrainLab iPlan Flow system is used to plan catheter trajectories based on predicted distributions using information obtained from a preoperative MRI.

This invention uses one mM of gadolinium as a surrogate tracer to identify the distribution of the poliovirus. This could be used for other drug infusions as well. The gadolinium is co-infused with the drug and various MRI sequences are used to quantify the distribution.

The entire volume of the agent to be delivered will be pre-loaded into a syringe by the investigational pharmacist and connected to the catheter under sterile conditions in the operating room or the NICU just prior to beginning of infusion. Due to the complexity of scheduling all of the necessary components for the infusion (operating room time, pharmacy time, and radiology appointments), a +1 day window has been built in to the study for the study drug infusion. This means that the infusion is allowed to start the following day after the biopsy/catheter placement. This will still be considered "day 0" in regards to the protocol and the timing of the subsequent events. At the time of virus injection, emergency drugs, including epinephrine and diphenhydramine will be available and the neurologic status, oxygen saturation, and cardiac rhythm will be monitored. Drug infusion will occur in the Neuro-Surgical Intensive Care Unit (NSCU) so that all other emergency facilities will be available. Patients will be treated with a prophylactic antibiotic such as nafcillin, a second-generation cephalosporin or vancomycin starting with the induction of anesthesia for the catheter placement.

Based on our own experience, previously published reports (19) and IRB- and FDA-approved trials using similar infusion techniques (IRB # 4774-03-4R0), patients will be infused at a rate of 500 µL/hr. A Medfusion 3500 infusion pump will be pre-programmed to a delivery rate of 500 µL/hr. The agent (which will be in a total volume of 10 mL to account for 'dead-space' of 3.3723 mL in the infusion system) will be loaded in a 20 mL syringe into the syringe pump at the initial onset to avoid any interruptions in the infusion. The total amount of the inoculum delivered to the patient will be 3 mL. The catheter itself (30 cm length, 1 mm interior diameter) cannot be preloaded with virus suspension. Therefore, the initial ~250 µL of infusion will be preservative-free salinein the 'dead-space' of the indwelling catheter. To account for this, the infusion pump will be programmed for delivery of 3.250 mL. The infusion will be performed using a Medfusion 3500 (Medex, Inc., Duluth, Ga.) syringe infusion pump. The virus injection procedure will be completed within 6.5 hrs. The catheter will be removed immediately following the delivery of PVSRIPO.

The infusion catheter (PIC 030) and infusion tubing (PIT 400) will be supplied by Sophysa, Inc. (Crown Point, Ind.). The Infusion Catheter Kit is a 30 cm clear, open-ended catheter (1.0 mm ID/2.0 mm OD) with 1 cm markings for 20 cm. The catheter comes with a 30 cm stainless steel stylet, a barbed female luer lock with cap and a stainless steel trocar. The Infusion Tubing Kit consists of a 3-way stopcock connector with air filter, 4 m of microbore tubing with antisiphon valve, a red, vented cap and a white luer lock cap. The catheter products are packaged sterile and non-pyrogenic and are intended for single (one-time) use only. The infusion will be performed using a Medfusion 3500 (Medex, Inc. Duluth, Ga.) syringe infusion pump.

Example 5

Results

The mechanism of immune checkpoint inhibitors is to release cytotoxic T cell function from events instigated by tumors that block their effector functions. Tumors engage a system of naturally existing 'brakes' that control cytotoxic T cells. To the tumor, this has the advantage of limiting the potential for the immune system to attack tumors that express mutant proteins and, therefore, represent a foreign signature. Immune checkpoint inhibitors reverse this tumor mechanism and release immune function.

We have found that PVSRIPO elicits an immune response that relies on cytotoxic T cells (CTL) attacking tumors. Thus combination of PVSRIPO with checkpoint inhibitors enhances the therapeutic effect. As shown below, PVSRIPO, indeed, works to treat tumors by inducing CTL responses.

We infected melanoma, breast, brain tumor, prostate cancer cells with PVSRIPO and collected the supernatant from dying/dead cells. The supernatant from the infected tumor cells was used to expose dendritic cells (a population of immune cells that is responsible for communicating with CTLs and coordinating their activation) from human subjects. As a consequence, the dendritic cells exhibited powerful signs of pro-inflammatory activation (i.e., the virus infection of the tumor cells produced soluble factors that promote the CTL activation functions of dendritic cells).

The activated dendritic cells were then co-cultivated with T cells (including CTLs) from the same human subject that donated the dendritic cells. The co-cultured T cells (including CTLs) were then co-cultivated with uninfected tumor cells from the same lines used for the infection step.

Figure 2:
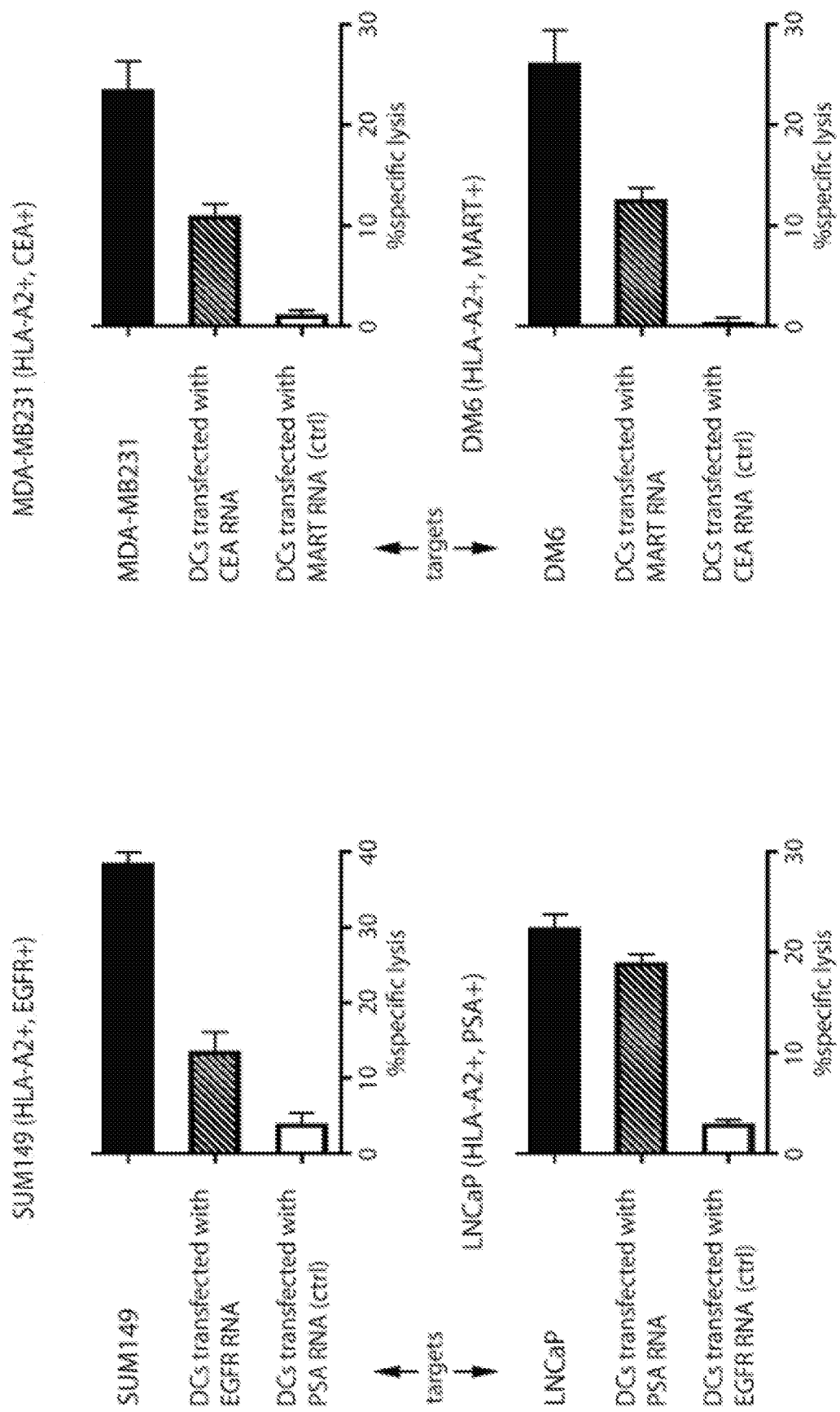
FIG. 2 shows results using four different tumor cell lines representing, breast, melanoma, and prostate cancers. DCs were seeded in dishes. Supernatant from onco-lysate was added to DC cultures and incubated. Supernatant was then removed and DCs were washed. DNase I-treated peripheral blood mononuclear cells (PBMCs) were incubated at 37° C. Non-adherent cells were harvested and stimulated with DCs loaded with poliovirus-induced tumor lysate at a responder cell to stimulator DC ratio of 10:1 in the presence of IL-7 in CTL stimulation media. T cells were harvested on day 12-14, counted and used as effector T cells in a europium-release CTL assay. Autologous DCs transfected with relevant and irrelevant tumor antigen-encoding mRNA were used as control targets. For DC control targets, mRNA-electroporated target cells were harvested, washed to remove all traces of media and labeled with europium (Eu). Alternatively, original target cells (Sum149, MDAMB231, LNCaP, or DM6) were labeled with Eu. Ten thousand europium-labeled targets (T) and serial dilutions of effector cells (E) at varying E:T ratios were incubated in 96-well V-bottom plates. The plates were centrifuged at for 3 minutes and incubated at 37° C. 50 µl of the supernatant was harvested and added to 150 µl of enhancement solution in 96-well flat-bottom plates and europium release was measured by time resolved fluorescence using the VICTOR3 Multilabel Counter (Perkin-Elmer). Specific cytotoxic activity was determined using the formula: % specific release= [(experimental release−spontaneous release)/(total release−spontaneous release)]×100. Spontaneous release of the target cells was less than 25% of total release by detergent. Spontaneous release of the target cells was determined by incubating the target cells in medium without T cells. All assays were done in triplicate, bars represent average % lysis and error bars denote SEM.

We observed high-level cytotoxicity of the activated CTLs against the tumor cells. See FIG. 2.

This experiment, in vitro, exemplifies what we believe happens in patients: virus infection elicits a series of events that ultimately leads to the generation of a CTL response against the tumor. This series of events can be enhanced synergistically with immune checkpoint inhibitors.

One of the natural existing 'brakes' on T cell function (immune checkpoints) is the PD1-PD-L1 link. Dendritic cells in tumor often are induced to express PD-L1, which then binds to PD1 on T cells to inhibit activation of the T cells.

We have demonstrated that dendritic cells exposed to PVSRIPO/PVSRIPO-tumor lysate increase PD-L1 expression. PD-1 or PD-L1 inhibitors, paradigmatic checkpoint inhibitors, prevent this effect and increase CTL activation by PVSRIPO oncolysis.

Example 6

Methods

Confluent 10 cm dishes of Sum149, MDAMB231, LNCaP, or DM6 cells were infected with mock (DMEM) or PVSRIPO (MOI 0.1) in AIMV medium for 48 hours. Supernatants were collected and cell debris was removed by centrifugation. Frozen PBMCs were thawed, washed in PBS and resuspended at $2\times10^8$ cells in 30 ml AIM-V media in T-150 tissue culture flasks (3). Cells were incubated for 1 h at 37° C. The non-adherent cells were harvested by rocking the flask from side to side to dislodge them. The adherent cells were replenished with 30 ml AIM-V supplemented with 800 U/ml human GM-CSF and 500 U/ml human IL-4, then incubated at 37° C. DCs were harvested on day 6, by collecting all non-adherent cells, followed by a cold PBS wash. Cells that were still adherent were dissociated with cell dissociation buffer. DCs were washed in AIMV medium, counted and seeded in 35 mm dishes at $1\times10^6$ cells per dish. Supernatant from onco-lysate was added to DC cultures and incubated for 24 hours. Supernatant was then removed and DCs were washed in AIMV medium. PBMCs were thawed and resuspended in PBS and treated with DNase I at 200 U/ml for 20 min at 37° C. DNase I-treated PBMCs were incubated for 1 h at 37° C., Non-adherent cells were harvested and stimulated with DCs loaded with poliovirus-induced tumor lysate at a responder cell to stimulator DC ratio of 10:1 in the presence of 25 ng/ml IL-7. All stimulations were done in RPMI 1640 with 10% FCS, 2 mM L-glutamine, 20 mM HEPES, 1 mM sodium pyruvate, 0.1 mM MEM non-essential amino acids, 100 IU/ml penicillin, 100 µg/ml streptomycin and 5×M 13-mercaptoethanol (CTL stimulation medium). The responder T-cell concentration was $2\times10^6$ cells/ml. IL-2 was added at 100 U/ml on day 3 and every 4-5 days for 12-14 days. T cells were maintained at $1-2\times10^6$ cells/ml in CTL stimulation medium. T cells were harvested on day 12-14, counted and used as effector T cells in a europium-release CTL assay. Autologous DCs transfected with tumor antigen-encoding mRNA were used as targets as controls. For DC target controls, mRNA-electroporated target cells (as designated in FIG. 2) were harvested, washed to remove all traces of media and labeled with europium (Eu). Alternatively original target cells (Sum149, MDAMB231, LNCaP, or DM6) were labeled with Eu. The Eu-labeling buffer (1 ml per target) contained 1 ml HEPES buffer (50 mM HEPES, 93 mM NaCl, 5 mM KCl, 2 mM $MgCl_2$, pH 7.4), 10 µl Eu (10 mM $EuCl_3.6H_2O$ in 0.01 N HCl), 5 µl DTPA (100 mM diethylenetriamine pentaacetate in HEPES buffer) and 4 µl DS (1% dextran-sulfate) (4) $5\times10^6$ target cells were resuspended in 1 ml of the europium-labeling buffer very gently and incubated on ice for 20 minutes. 30 µl of CaCl2 solution (100 mM) was then added to the labeled cells, mixed and the cells were incubated for another 5 minutes on ice. 30 ml of Repair buffer (HEPES buffer with 10 mM glucose, 2 mM $CaCl_2$) was added to the cells and the cells were centrifuged at 1000 rpm for 10 minutes. Cells were counted and $5\times10^6$ cells were washed 4 times with Repair buffer. After the final wash the cells were resuspended in CTL stimulation medium without penicillin-streptomycin at $10^5$ cells/ml. Ten thousand europium-labeled targets (T) and serial dilutions of effector cells (E) at varying E:T ratios were incubated in 200 µl of CTL stimulation medium with no penicillin-streptomycin in 96-well V-bottom plates. The plates were centrifuged at 500×g for 3 minutes and incubated at 37° C. for 4 hours. 50 µl of the supernatant was harvested and added to 150 µl of enhancement solution (Wallac, Perkin-Elmer) in 96-well flat-bottom plates and europium release was measured by time resolved fluorescence using the VICTOR3 Multilabel Counter (Perkin-Elmer). Specific cytotoxic activity was determined using the formula: % specific release=[(experimental release−spontaneous release)/(total release−spontaneous release)]×100. Spontaneous release of the target cells was less than 25% of total release by detergent. Spontaneous release of the target cells was determined by incubating the target cells in medium without T cells. All assays were done in triplicate, bars represent average % lysis and error bars denote SEM.

Example 7

PVSRIPO antitumor efficacy may be aided by the virus' ability to elicit strongly immunogenic type 1 interferon (IFN) responses in infected tumor cells and in infected antigen-presenting cells (dendritic cells, macrophages, microglia). However, although type 1 IFN responses are highly desirable as mediators of immunotherapy, they also engage known immune checkpoints that can dampen the anti-neoplastic immune response elicited by PVSRIPO, e.g., PD-L1. Therefore, to maximize PVSRIPO immunotherapy, combination with immune checkpoint blockade may be indicated. This is evident in assays in immune-competent, syngeneic glioma tumor models (e.g., CT2A). See Martinez-Murillo et al., *Histol. Histopathol.* 12:1309-26 (2007).

Figure 3A:
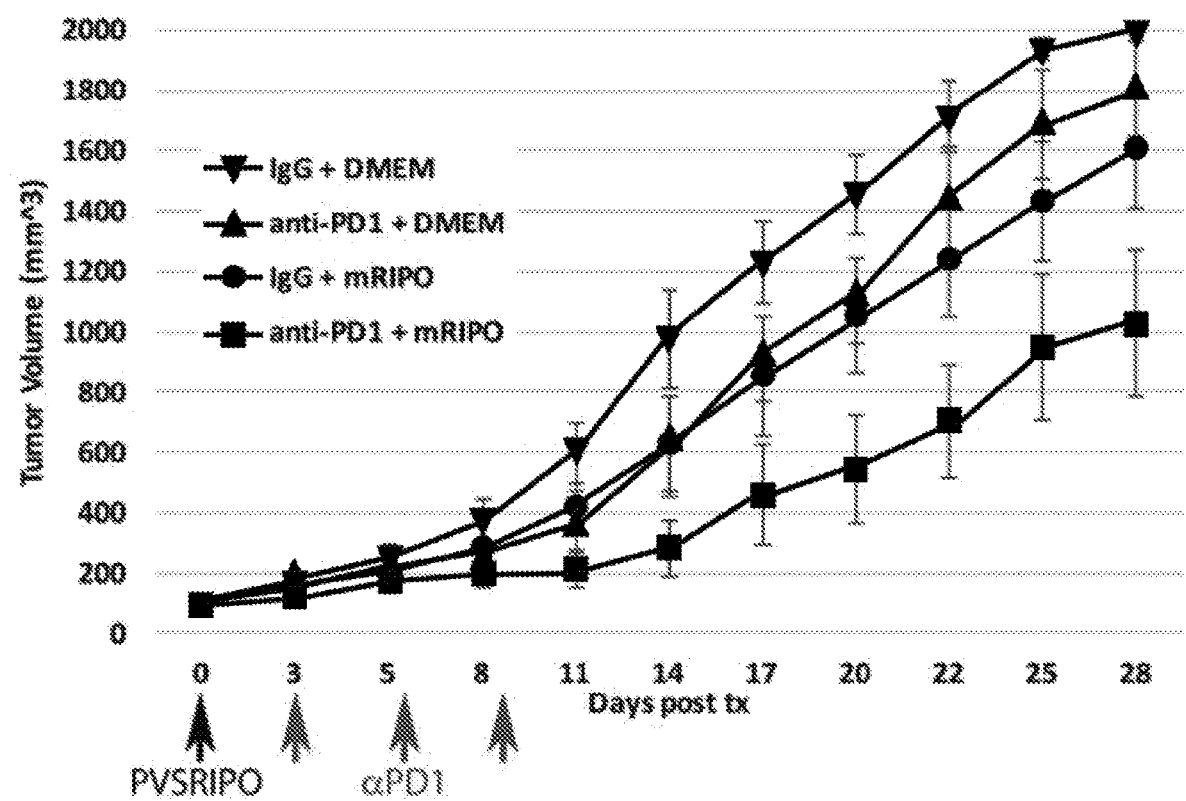
Figure 3B:
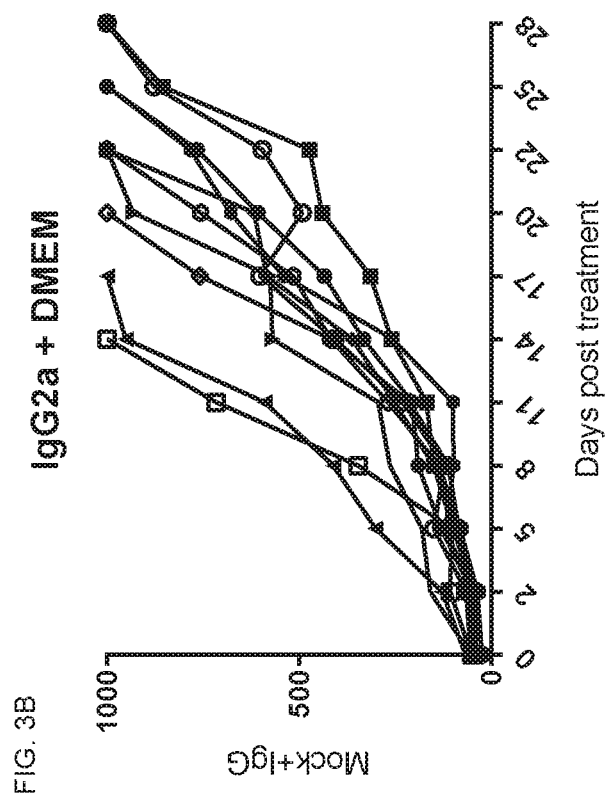
Figure 3C:
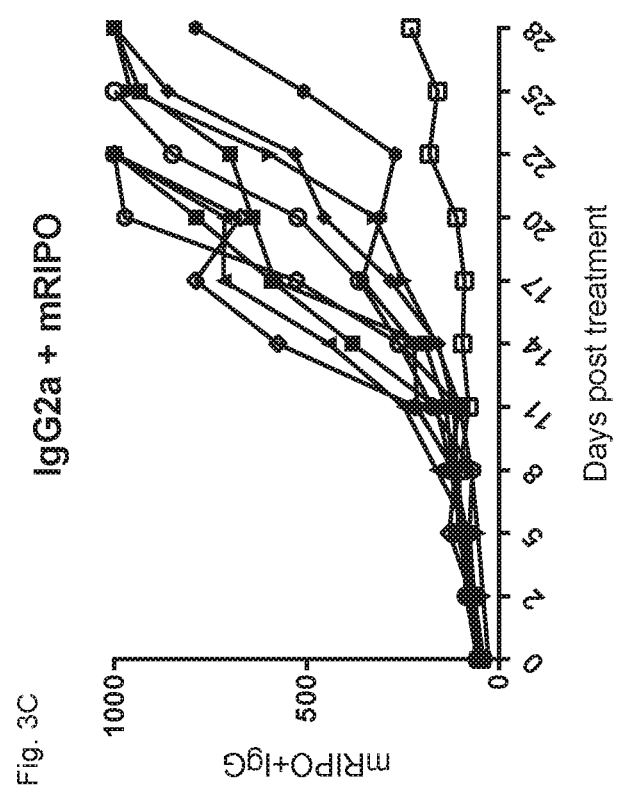

We implanted subcutaneous CT2A gliomas in C57B16 mice transgenic for the poliovirus receptor CD155. The CT2A cells used to initiate tumors were previously transduced with CD155 (to enable PVSRIPO infection analogous to human cells). Four groups of tumor-bearing animals (n=10) were treated as follows: Group I: DMEM (vehicle to control for virus)+IgG (to control for anti-PD1); Group II: single intra-tumoral injection of PVSRIPO+IgG; Group III: single intra-tumoral injection of DMEM+anti-PD1; Group IV: single intra-tumoral injection of PVSRIPO+anti-PD1. Anti-PD1 was given in three installments (days 3, 6, 9) by intraperitoneal injection. Results are shown in FIG. 3; the top panel shows the group results and the bottom panels shows results for individual mice.

Both PVSRIPO and anti-PD1 had significant anti-tumor effects individually (top panel). The combination of the two agents had added therapeutic effects, suggesting mechanistic synergy (top panel). Importantly, durable tumor remission (indicated by flat-lining of the tumor response curves at very low tumor volumes) was only achieved with the combination treatment.

REFERENCES

The disclosure of each reference cited is expressly incorporated herein.
1. Castriconi R, A Daga, A Dondero, G Zona, P L Poliani, et al. 2009. NK cells recognize and kill human glioblastoma cells with stem cell-like properties. J Immunol 182:3530-39.
2. de Breyne S, Y Yu, A Unbehaun, T V Pestova, C U Hellen. 2009. Direct functional interaction of initiation factor eIF4G with type 1 internal ribosomal entry sites. Proc Natl Acad Sci USA 106:9197-202.
3. Dobrikova E Y, T Broadt, J Poiley-Nelson, X Yang, G Soman, et al. 2008. Recombinant oncolytic poliovirus eliminates glioma in vivo without genetic adaptation to a pathogenic phenotype. Mol Ther 16:1865-72.
4. Dobrikova E Y, C Goetz, R W Walters, S K Lawson, J O Peggins, et al. 2012. Attenuation of neurovirulence, biodistribution, and shedding of a poliovirus:rhinovirus chimera after intrathalamic inoculation in Macaca fascicularis. J Virol 86:2750-9.
5. Erickson B M, N L Thompson, D C Hixson. 2006. Tightly regulated induction of the adhesion molecule nec1-5/CD155 during rat liver regeneration and acute liver injury. Hepatology 43:325-34.

6. Goetz C, E Dobrikova, M Shveygert, M Dobrikov, M Gromeier. 2011. Oncolytic poliovirus against malignant glioma. Future Virol 6:1045-58.
7. Goetz, C, R G Everson, L Zhang, M Gromeier. 2010. MAPK signal-integrating kinase controls cap-independent translation and cell type-specific cytotoxicity of an oncolytic poliovirus. Mol Ther 18:1937-46.
8. Gromeier M, L Alexander, E Wimmer. 1996. Internal ribosomal entry site substitution eliminates neurovirulence in intergeneric poliovirus recombinants. Proc Natl Acad Sci USA 93:2370-5.
9. Gromeier M, B Bossert, M Arita, A Nomoto, E Wimmer. 1999. Dual stem loops within the poliovirus internal ribosomal entry site control neurovirulence. J Virol 73:958-64.
10. Gromeier M, S Lachmann, M R Rosenfeld, P H Gutin, E Wimmer. 2000. Intergeneric poliovirus recombinants for the treatment of malignant glioma. Proc Natl Acad Sci USA 97:6803-8.
11. Gromeier M, D Solecki, D D Patel, E Wimmer. 2000. Expression of the human poliovirus receptor/CD155 gene during development of the central nervous system: implications for the pathogenesis of poliomyelitis. Virology 273:248-57.
12. Iwasaki A, R Welker, S Mueller, M Linehan, A Nomoto, et al. 2002. Immunofluorescence analysis of poliovirus receptor expression in Peyer's patches of humans, primates, and CD155 transgenic mice: implications for poliovirus infection. J Infect Dis 186:585-92.
13. Joshi S, S Kaur, A J Redig, K Goldsborough, K David, et al. 2009. Type I IFN-dependent activation of Mnk1 and its role in the generation of growth inhibitory responses. Proc Natl Acad Sci USA 106:12097-102.
14. Masson D, A Jarry, B Baury, P Blanchardie, C Laboisse, et al. 2001. Overexpression of the CD155 gene in human colorectal carcinoma. Gut 49:236-40.
15. Merrill M K, G Bernhardt, J H Sampson, C J Wikstrand, D D Bigner, et al. 2004. Poliovirus receptor CD155-targeted oncolysis of glioma. Neuro-oncol 6:208-17.
16. Merrill M K, E Y Dobrikova, M Gromeier. 2006. Cell-type-specific repression of internal ribosome entry site activity by double-stranded RNA-binding protein 76. J Virol 80:3147-56.
17. Merrill M K, M Gromeier. 2006. The double-stranded RNA binding protein 76:NF45 heterodimer inhibits translation initiation at the rhinovirus type 2 internal ribosome entry site. J Virol 80:6936-42.
18. Nakai R, Y Maniwa, Y Tanaka, W Nishio, M Yoshimura, et al. 2010. Overexpression of Nec1-5 correlates with unfavorable prognosis in patients with lung adenocarcinoma. Cancer Sci 101:1326-30.
19. Neplioueva V, E Y Dobrikova, N Mukherjee, J D Keene, M Gromeier. 2010. Tissue type-specific expression of the DRBP76 and genome-wide elucidation of its target mRNAs. PloS One 5:e11710.
20. Ochiai H, S A Campbell, G E Archer, T A Chewning, E Dragunsky, et al. 2006. Targeted therapy for glioblastoma multiforme neoplastic meningitis with intrathecal delivery of an oncolytic recombinant poliovirus. Clin Can Res 12:1349-54.
21. Ochiai H, S A Moore, G E Archer, T Okamura, T A Chewning, et al. 2004. Treatment of intracerebral neoplasia and neoplastic meningitis with regional delivery of oncolytic recombinant poliovirus. Clin Can Res 10:4831-8.
22. Takai Y, J Miyoshi, W Ikeda, H Ogita. 2008. Nectins and nectin-like molecules: roles in contact inhibition of cell movement and proliferation. Nat Rev Mol Cell Biol 9:603-15.
23. Toyoda H, J Yin, S Mueller, E Wimmer, J Cello. 2007. Oncolytic treatment and cure of neuroblastoma by a novel attenuated poliovirus in a novel poliovirus-susceptible animal model. Cancer Res 67:2857-64.
24. Wahid R, M J Cannon, M Chow. 2005. Dendritic cells and macrophages are productively infected by poliovirus. J Virol 79:401-9.

The invention claimed is:

1. A method of treating a tumor in a patient to achieve a therapeutic anti-tumor effect, wherein the tumor expresses NECL5 (nectin-like protein 5), comprising:
    administering to the patient a chimeric poliovirus construct comprising a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame; and
    administering an immune checkpoint inhibitor to the patient, whereby the patient is treated.
2. The method of claim 1 wherein the tumor is a glioblastoma.
3. The method of claim 1 wherein the tumor is an astrocytoma or an oligodendroglioma.
4. The method of claim 1 wherein the tumor is an astro-oligodendroglioma.
5. The method of claim 1 wherein the tumor is a renal cell carcinoma.
6. The method of claim 1 wherein the tumor is urostate tumor.
7. The method of claim 1 wherein the tumor is a bladder tumor.
8. The method of claim 1 wherein the tumor is an esophagus and/or a stomach tumor.
9. The method of claim 1 wherein the tumor is a pancreas tumor.
10. The method of claim 1 wherein the tumor is a colorectal tumor.
11. The method of claim 1 wherein the tumor is a liver or gall bladder tumor.
12. The method of claim 1 wherein the tumor is a breast tumor.
13. The method of claim 1 wherein the tumor is a medulloblastoma.
14. The method of claim 1 wherein the tumor is a lung tumor.
15. The method of claim 1 wherein the tumor is a head and neck tumor.
16. The method of claim 1 wherein the tumor is a melanoma.
17. The method of claim 1 wherein the tumor is a sarcoma.
18. The method of claim 1 wherein the chimeric poliovirus construct is administered by intracerebral infusion with convection enhanced delivery.
19. The method of claim 1 wherein the chimeric poliovirus construct is administered directly to the tumor.
20. The method of claim 1 wherein the checkpoint inhibitor is an anti-PD-1 antibody.
21. The method of claim 1 wherein the checkpoint inhibitor is an anti-PDL-1 antibody.
22. The method of claim 1 wherein the checkpoint inhibitor is an anti-CTLA4 antibody.

23. The method of claim 1 wherein the checkpoint inhibitor is an anti-LAG-3 antibody.

24. The method of claim 1 wherein the checkpoint inhibitor is an anti-TIM-3 antibody.

25. The method of claim 1 wherein the immune checkpoint inhibitor is administered within 30 days of administering the chimeric poliovirus construct.

26. The method of claim 1 wherein the immune checkpoint inhibitor is administered within 7 days of administering the chimeric poliovirus construct.

27. The method of claim 1 wherein the chimeric poliovirus construct is PVS-RIPO.

\* \* \* \* \*

UNITED STATES PATENT AND TRADEMARK OFFICE
CERTIFICATE OF CORRECTION

PATENT NO. : 10,744,170 B2  
APPLICATION NO. : 15/768147  
DATED : August 18, 2020  
INVENTOR(S) : Bigner et al.

Page 1 of 1

It is certified that error appears in the above-identified patent and that said Letters Patent is hereby corrected as shown below:

In the Specification

Column 1, Lines 3-7:  
Please delete:  
"This invention was made using funds provided by the United States government. The U.S. government retains certain rights according to the terms of grants from the National Institutes of Health R01 CA87537, P50 NS20023, P50 CA190991, R01 CA124756, and R01 CA140510."

And insert:  
--This invention was made using funds provided by the United States government. The U.S. government retains certain rights according to the terms of grants from the National Institutes of Health R01 CA87537, P50 NS20023, P50 CA190991, R01 CA124756, and R01 CA140510, and from Department of Defense Breast Cancer Research Program award number W81XWH-16-1-0354.--

Signed and Sealed this  
Fifteenth Day of December, 2020

Andrei Iancu  
*Director of the United States Patent and Trademark Office*